United States Patent [19]
Gilby

[11] Patent Number: 5,194,915
[45] Date of Patent: Mar. 16, 1993

[54] PHOTOMETRIC APPARATUS AND PROCESS

[75] Inventor: Anthony C. Gilby, Foxborough, Mass.

[73] Assignee: Millipore Corporation, Bedford, Mass.

[21] Appl. No.: 585,465

[22] Filed: Sep. 20, 1990

[51] Int. Cl.⁵ .......................... G01J 3/30; F21V 9/16
[52] U.S. Cl. ................................. 356/318; 250/458.1
[58] Field of Search ............... 356/73, 317, 318, 39, 356/440; 250/458.1, 459.1, 461.1, 461.2

[56] References Cited

U.S. PATENT DOCUMENTS

| | | | |
|---|---|---|---|
| 4,515,274 | 5/1985 | Hollinger et al. | 356/39 |
| 4,867,559 | 9/1989 | Bach | 356/440 |
| 4,934,811 | 6/1990 | Watts et al. | 356/319 |

Primary Examiner—F. L. Evans
Assistant Examiner—K. P. Hantis
Attorney, Agent, or Firm—Paul J. Cook; Andrew T. Karnakis

[57] ABSTRACT

A photometric apparatus is provided for analyzing a sample liquid capable of fluorescing when exposed to excitation light. The sample liquid, surrounded by a sheath liquid under conditions of laminar flow to form an interface between the sample liquid and the sheath is passed through a cell conduit. An excitation light is directed axially into the sample liquid and is totally internally reflected at the interface with the sheath liquid. The sample fluoresces in response to the excitation light and fluorescent emission is observed through the sheath liquid.

8 Claims, 2 Drawing Sheets

PHOTOMETRIC APPARATUS AND PROCESS

BACKGROUND OF THE INVENTION

This invention relates to a photometric apparatus useful in liquid chromatography (LC) or capillary electrophoresis (CE), and more particularly to such an apparatus which allows efficient fluorescence measurement of small samples while preventing excitation beam light rays from impinging on the cell walls, or unwanted fluorescent signals from affecting the measurement.

In an LC or CE system, detection of sample constituents can be effected by passing the eluent from the column through a small volume sample cell, and passing excitation light through the cell to cause the sample to fluoresce. The fluorescent light emitted, from the cell at right angles to the excitation beam, is measured to determine the characteristics of the sample.

In practice, fluorescence detection from a small volume of sample is limited by the presence of the walls and windows of the sample cell. The walls and windows scatter light at various wavelengths:

1. At the wavelength of the exciting light (Raleigh scattering).
2. At Raman shifted wavelengths characteristic of the cell material.
3. Emission over wide and unpredictable wavelength ranges due to adsorption onto, and penetration into, the cell walls and windows by contaminating fluorescent species. All these contribute to unwanted stray light which cannot be satisfactorily rejected by the emission monochromator or spectrograph. The result is an elevated base line, and noise on the photodetector of photomultiplier signal, raising the minimum detection limit of the species of interest.

In conventional fluorescence systems with small sample volumes, unwanted stray light is minimized by focussing the excitation beam in the center of the sample cell and using masks to collect fluorescent emission only from the center of the cell. However, this means that only a part of the sample can be analyzed, leading to elevated limits of detection.

It has been proposed in U.S. Pat. No. 3,788,744 to provide an apparatus for optically analyzing small particles in a thin liquid stream. The thin stream is surrounded by a flowing liquid sheath in order to prevent contact of the thin stream with the walls of the cell through which it is passed. The particles are caused to fluoresce by an excitation laser beam which is directed transverse the direction of stream flow and the fluorescence is detected at right angles to both. Since the light beam is transverse the direction of the stream flow, the beam traverses the sheath liquid and strikes the walls of the stream conduit thereby causing the problems set forth above.

It has also been proposed in U.S. Pat. No. 3,984,307 to sort particles in a thin stream surrounded by a sheath stream by means of an excition light which permits characterizing the particles to be sorted. However, the excitation light beam also is positioned transverse the thin stream with the attendant problems disclosed above.

It has also been proposed by Fujiwara et al, Anal. Chem. Volume 60, page 1065, 1988 to utilize a high refractive index solvent such as carbon disulfide which is passed through a silica capillary tube but without a sheath stream. A laser light is guided axially by the high refractive index liquid and fluorescent light emerges at the end of the tube along with residual laser light to be filtered and detected. This arrangement does not eliminate the problems associated with light striking the cell wall nor does it utilize total internal reflection to separate the excitation light from the fluorescent emission. Additionally, the requirement of a mobile phase with a refractive index higher than the silica capillary places a severe limitation on possible applications.

Accordingly, it would be desirable to provide a fluorometer capable of detecting induced fluorescence of a sample wherein neither the sample nor excitation light beam contacts the walls or window of a sample cell, and in which full sample volume is measured to achieve maximum sensitivity.

SUMMARY OF THE INVENTION

The present invention is based on the discovery that a liquid sheath of lower refractive index surrounding the sample stream, under conditions of laminar flow, can create an optical waveguide of the LC or CE eluting stream. An excitation light beam directed axially along the flowing stream is guided within the sample by total internal relection at the sample/sheath boundary, much as light is guided along an optical fiber by total internal relection at the boundary between the core and cladding. By this means, the cell walls and windows are effectively removed from the system, and because the sheath is continuously renewed, contamination by previous samples is no longer a problem. This guided wave structure contains the excitation beam within the sample stream with minimal contact with the sheath liquid. To the extent that the liquids are non-scattering, excitation light is prevented from reaching the emission optics. On the other hand, fluorescent light, emitted in all directions, will escape from the structure and be detected.

With proper cell design, the excitation beam illuminates all the sample contained in an eluting chromatographic or electrophoretic peak, thereby increasing the fluorescent emission and leading to improved detection limits.

To create the sheathed flow, a sample stream such as a stream obtained as the effluent from an LC or CE column is directed into a central conduit section of a dual conduit while a liquid sheath stream is directed into an outer conduit section surrounding the central conduit section of the dual conduit. Both liquid streams exit the dual conduit and enter a sample cell where the sheath stream surrounds the sample stream under conditions of laminar flow such as by controlling conventional pumps, (not shown) or by gravity or, in the case of CE, by electro-osmosis. A source of excitation light is positioned to direct an excitation light beam axially and within the sample stream in the sample cell. The sample stream is caused to fluoresce when exposed to the excitation light beam. The refractive index of the sample stream is maintained greater than the refractive index of the sheath stream in order to form an interface between the two streams and retain the excitation light beam within the sample stream by total internal reflection without striking the walls of the sample cell.

DESCRIPTION OF SPECIFIC EMBODIMENTS

In accordance with this invention, a dual layer liquid flow stream is provided wherein a sample liquid is positioned within a central portion of the stream, while a sheath liquid, of lower refractive index, is provided which surrounds the sample liquid. Under conditions of laminar flow a smooth boundary exists between the sample and sheath liquids through the region of interest. A narrow beam of light is directed along the axis of the flowing stream, so that it enters the sample liquid and is contained within it by total internal reflection at the boundary between the sample and sheath liquid. The flowing streams therefore act as an optical wave guide for a beam of light which excites fluorescence in the sample. Fluorescent light which escapes through the sheath liquid is collected and measured to provide the desired analytical information. The dual layer liquid is formed in a dual conduit having a central conduit positioned within an outer conduit. The sheath liquid is introduced into the outer conduit and the sample liquid is introduced into the central conduit. The sample to be detected is dissolved such as the stream eluting from a liquid chromatograph or CE column. The sheath liquid and sample liquid exit the dual conduit into a sample cell conduit under laminar flow conditions so that the two liquids do not admix while an interface is maintained between the two liquids. A source of excitation light is positioned downstream of the dual layer liquid so that light is directed into the sample liquid but no into the outer sheath liquid. Sample within the sample stream is caused to fluoresce as a response to being exposed to the excitation light. Since the excitation light is retained within the sample stream by total internal reflection at the sample liquid-sheath liquid interface and since the fluorescence response light is omnidirectional, the fluorescent light passes through the sheath liquid so that it can be observed through a portion of the cell conduit wall which is transparent to the fluorescent light. Thus, the observed light is not adversely affected by spurious signals such as scattering and fluorescence which can occur when the excitation light intersects with the cell walls or windows. In addition, since the sample liquid does not contact the walls of the cell conduit, contamination of the walls of the cell conduit, with sample is avoided. In a preferred embodiment, only a portion of the cell conduit is transparent to the fluorescent light while the remainder of the cell conduit walls are mirrored to reflect fluorescent light. In this embodiment, the fluorescent signal observed on one side of the sample cell is greatly intensified.

Figures 1, 2:
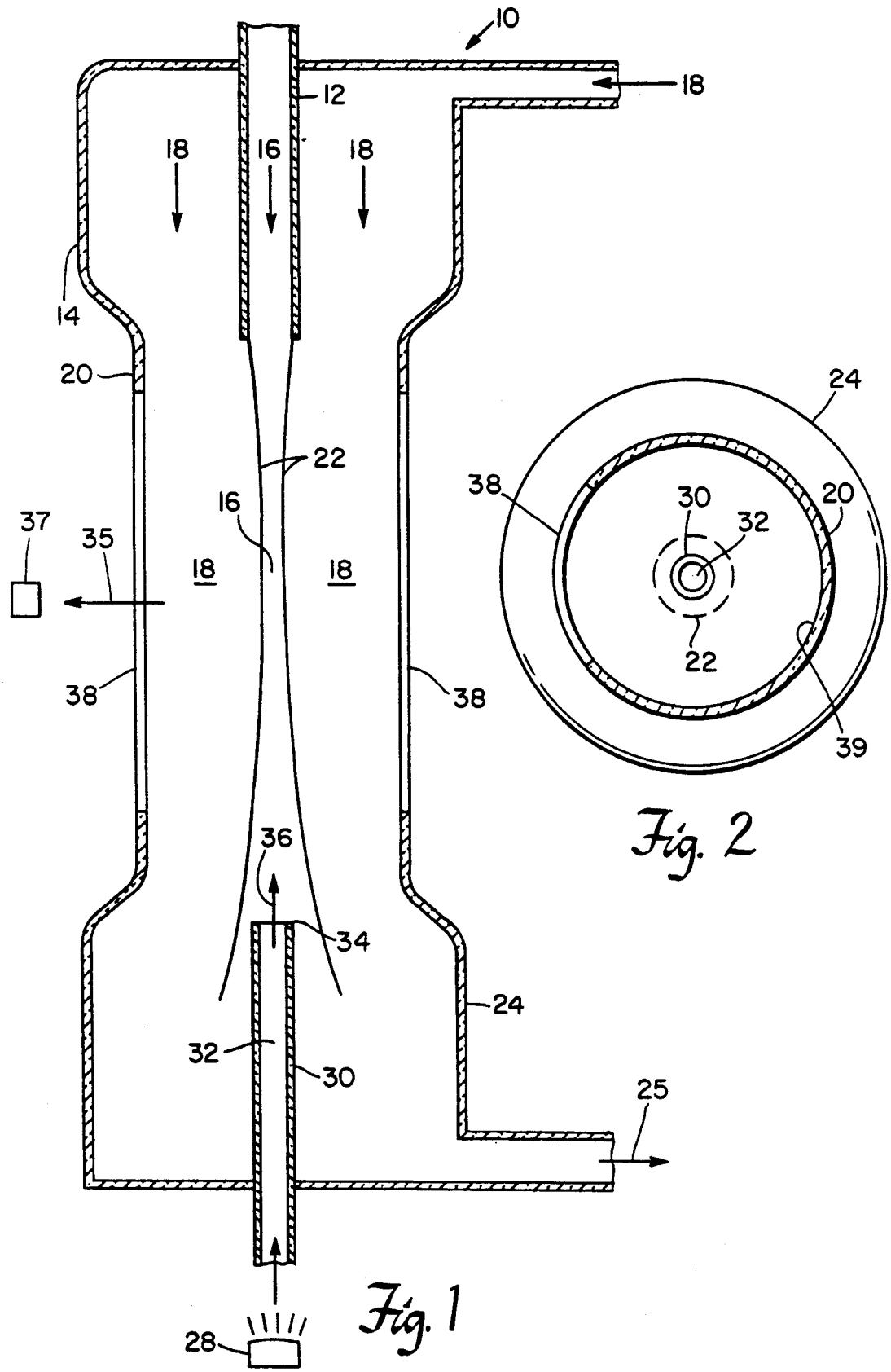
FIG. 1 is a cross-sectional side view of the apparatus of this invention.
FIG. 2 is a cross-sectional view taking along line 2—2 of FIG. 1.
Figure 3:
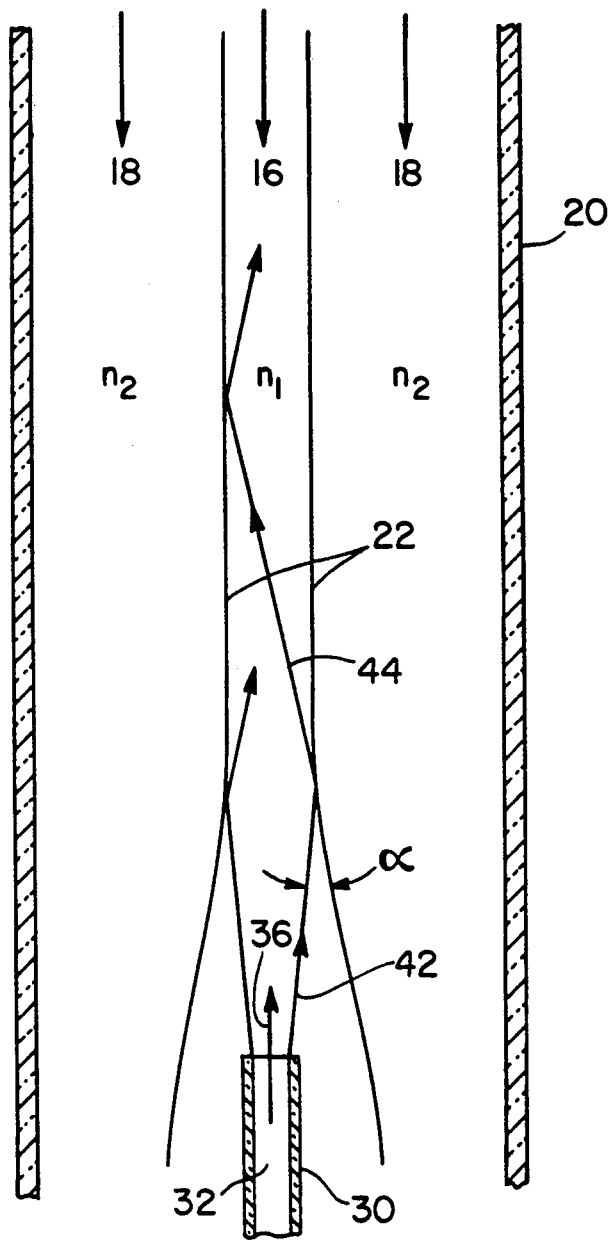
FIG. 3 is an illustration of the refractive index requirements of the liquids utilized herein.

Referring to FIGS. 1 and 2, a dual conduit 10 is provided which comprises a central conduit 12 and an outer conduit 14. A sample stream 16 passes through conduit 12 while a sheath stream 18 passes through conduit 14. The sample stream 16 and sheath stream 18 emerge from the dual conduit 10 under conditions of laminar flow and enter sample cell conduit 20. In sample cell conduit 20, the sheath stream 18 surrounds sample stream 16. The two streams form an interface 22 which functions to totally internally reflect excitation light to maintain it within sample stream 16 and to prevent it from entering sheath stream 18. The sample stream 16 and sheath stream 18 exit the cell conduit 20 into outlet conduit 24 as shown by arrow 25. It is preferred that the outer conduit 24 has a larger diameter than cell conduit 20 so that sheath liquid 18 does not enter the optical path of light emerging from optical fiber 30. Light from source 28 is conducted along the core 32 of optical fiber 30 to emerge at fiber end 34 and to be directed axially, as shown by arrow 36 into the sample stream 16 located within cell conduit 20. The cell conduit 20 is provided with a window 38 which is transparent to the fluorescent light 35 produced by the sample in response to exposure from excitation light emitted from light source 28 which is detected by detector 37. The excitation light is conveniently laser light from a conventional source which is directed into optical fiber 30. In a preferred embodiment, surface 39 of cell conduit 20 is mirrored to reflect the fluorescent light produced by the sample (FIG. 2). Referring to FIG. 3, the function of the interface between the sample liquid and sheath liquid is shown. In order for the excitation light beam to be guided, a certain minimum refractive index difference, n, must exist between sample 16 (index $n_1$) and sheath liquid 18 (index $n_2$). If the largest angle between light rays 42 in excitation beam 36 and sample/sheath boundary 22 is a then, by Snell's Law, the least refractive index difference (at the wavelength of the excitation beam) to ensure total internal reflection of ray 42 to ray 44 is:

$$\delta n = n_1 - n_2 = n_1 - n_1 sin(90 - \alpha) = n_1(1 - cos\alpha)$$

For example, if $\alpha = 5°$ and $n_1 = 1.350$, $\delta n$ must be at least 0.005.

It is advantageous to select $\delta n$ near the minimum needed to guide the excitation light, so as to allow as much of the fluorescent light as possible to escape from the sample stream. The value of $\alpha$ will vary depending on the nature of light source 28 and optical fiber 30 and the shape of boundary 22 established between the sample and sheath flow liquids, parameters which are dictated by the particular cell design and flow rates chosen. When the refractive indices are controlled in this manner, the excitation beam does not exit into the sheath liquid, nor does it strike the wall of the conduit through which the dual layer liquid is passed. It should be noted that even if some diffusion occurs between sample liquid 16 and sheath liquid 18, the refractive index gradient at the boundary will cause rays 42 to curve back and be guided within the sample liquid. That is, the wave guiding properties of the dual layer liquid will be more analogous to those of a graded index optical fiber than a step index optical fiber.

I claim:
1. Apparatus for measuring fluorescence from a liquid sample which comprises
   a dual conduit means having a central conduit positioned within an outer conduit,
   said outer conduit having an inlet and an outlet,
   at least a portion of a wall of said outer conduit being transparent to fluorescent radiation,
   means for introducing a first liquid through said outer conduit,
   means for introducing a liquid sample through said central conduit and into contact with said first liquid within said outer conduit,
   means for effecting laminar flow of said first liquid and said liquid sample through said outer conduit so that said first liquid forms a flowing sheath around said liquid sample,
   means for continuously removing said flowing sheath and said liquid sample from said outer conduit under conditions of laminar flow thereby to prevent contamination of said liquid sample,
a light source means to direct excitation from said light source axially into said outer conduit and into said liquid sample,
and means for detecting fluorescence from said sample,
said liquid sample stream having a refractive index higher than the refractive index of the first liquid at the wavelength of the excitation light.

2. The apparatus of claim 1 wherein said light source comprises a laser and said excitation light is conducted to said outer conduit by an optical fiber.

3. The apparatus of claim 2 wherein said optical fiber is positioned axially at the outlet of said outer conduit.

4. The apparatus of any one of claims 1, 2 or 3 wherein a portion of said outer conduit not transparent to fluorescent radiation is formed of a surface which reflects fluorescent radiation.

5. A process for measuring fluorescence from a liquid sample which comprises:
passing said liquid sample through a central conduit of a dual conduit comprising said central conduit positioned within an outer conduit,
passing a first liquid through said outer conduit,
passing said liquid sample and said first liquid to form a flowing sheath of said first liquid around said liquid sample within said outer conduit while controlling the refractive indices of said first liquid and said liquid sample such that light axially introduced into said outer conduit is guided within said sample,
continuously removing said flowing sheath and said liquid sample from said outer conduit thereby to prevent contamination of said liquid sample,
directing an excitation light axially into the sample within said outer conduit to cause said sample liquid to fluoresce and
detecting fluorescent energy from said sample liquid.

6. The apparatus of any one of claims 1, 2 or 3 wherein said liquid sample is selected from the group consisting of a liquid chromatography column effluent and a capillary electrophoresis column effluent.

7. The apparatus of any one of claims 1, 2 or 3 wherein a portion of said outer conduit not transparent to fluorescent radiation is formed of a surface which reflects fluorescent radiation and wherein said liquid sample is selected from the group consisting of a liquid chromatography effluent and a capillary electrophoresis column effluent.

8. The process of claim 5 wherein said liquid sample is selected from the group consisting of a liquid chromatography column effluent and a capillary electrophoresis column effluent.

* * * * *